United States Patent [19]

Spence

[11] 4,302,216

[45] Nov. 24, 1981

[54] ANTI-STATIC ADDITIVES

[75] Inventor: James R. Spence, Warrenville, Ill.

[73] Assignee: Standard Oil Company (Indiana), Chicago, Ill.

[21] Appl. No.: 124,095

[22] Filed: Feb. 25, 1980

Related U.S. Application Data

[60] Division of Ser. No. 900,102, Apr. 26, 1978, Pat. No. 4,252,542, which is a continuation-in-part of Ser. No. 810,378, Jun. 27, 1977, abandoned.

[51] Int. Cl.$^3$ .......................... C10L 1/18; C10L 1/22
[52] U.S. Cl. ........................................... 44/71; 44/72; 44/DIG. 2; 260/513 N
[58] Field of Search ...................... 44/71, 72, DIG. 2; 260/513 N

[56] References Cited

U.S. PATENT DOCUMENTS

| | | | |
|---|---|---|---|
| 3,826,633 | 7/1974 | Coon | 44/72 |
| 3,932,288 | 1/1976 | Hoke | 44/72 |
| 3,951,614 | 4/1976 | Horner et al. | 44/71 |
| 4,113,443 | 9/1978 | Spence | 44/72 |

FOREIGN PATENT DOCUMENTS 1464331  3/1969  Belgium .
1101040  1/1968  United Kingdom .

Primary Examiner—Jacqueline V. Howard
Attorney, Agent, or Firm—Mark DiPietro; William T. McClain; William H. Magidson

[57] ABSTRACT

An amino methylenesulfonic acid comprising the reaction product of an amine compound (eg) a substituted succinimide containing free primary or secondary nitrogen atoms or a compound of the formula $R_1NH-CH_2CH_2CH_2NH_2$ or $RNH_2$ wherein R and $R_1$ have 1 to 25 carbon atoms; a compound of the formula

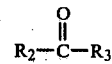

wherein $R_2$ is a hydrogen or a methyl group and $R_3$ is a hydrogen or an alkyl group having from about 1 to 7 carbon atoms and sulfur dioxide; which can be alternatively reacted with a polyfunctional crosslinking agent; and mixtures of the amino-methylene sulfonic acid with a nitrogen compound adduct of a maleic anhydride olefin copolymer.

5 Claims, No Drawings

ANTI-STATIC ADDITIVES

This is a division of application Ser. No. 900,102, filed Apr. 26, 1978, now U.S. Pat. No. 4,252,542 which is a continuation-in-part of Ser. No. 810,378, filed June 27, 1977, now abandoned.

Generation of static electricity on hydrocarbons is very dangerous. Numerous explosions and fires have been caused by static sparks resulting from charges generated on hydrocarbons. Commonly, static charges are generated on materials which have low conductivities. Low conductivities commonly result from the general purity of many hydrocarbons. Commonly, hydrocarbon fuels are materials which have low conductivities and are susceptible to static charge generation. Aviation jet fuel, for example, often can have conductivity of less than about one picosiemen. A minimum conductivity of fifty picosiemens is generally considered necessary to dissipate the static charges generated on the hydrocarbon.

Static charges are commonly built up during storage and transfer of fluid hydrocarbons in metal pipes and containers. If the conductivity of the hydrocarbons is high, the static charges dissipate quickly. When the conductivities are low, the static charge dissipates very slowly. Sparks occur when the static is generated faster than the charge can be dissipated. Once the voltage of the static charge passes a certain level, called the "breakdown potential," believed to be about 30,000 volts, a spark occurs.

Prior art patents which disclose anti-static compositions are U.S. Pat. Nos. 3,449,097; 3,534,975; 3,578,421; 3,677,724; 3,917,466; and 4,029,480.

U.S. Pat. No. 3,844,732 discloses fuel detergents comprising the reaction product of a hydrocarbyl (polybutene) substituted amine compound having at least 30 carbon atoms, in aldehyde and sulfur dioxide. These compounds are produced by first reacting a polyamine with an olefin having greater than 30 carbon atoms, and then reacting the polyamine-olefin reaction product with a carbonyl compound and sulfur dioxide. The use of succinic anhydride adducts or the use of polyfunctional crosslinking agents are not disclosed. Non-crosslinked compounds of this type having large (greater than 30 carbon atoms) hydrocarbon group substituted amines have minimal anti-static activity.

U.S. Pat. No. 3,677,724 discloses anti-static compositions for hydrocarbons containing (1) a maleamic acid of a beteropolymer of maleic acid anhydride and a monoolefin having at least two carbon atoms per molecule and an unsubstituted primary amine containing between about 4 and about 30 carbon atoms per molecule, glycine or aniline and (2) an alkyl vinyl ether/maleic anhydride copolymer; or the reaction product of an amine salt of the maleamic acid of (1) and an alkyl vinyl ether/maleic anhydride copolymer. Mixtures of these composition and the compositions disclosed herein can be advantageously used as anti-static compositions.

The compositions currently in use as anti-static agents often suffer the disadvantage that some fuels which suffer from static caused ignition and explosion are not protected adequately by costeffective amounts of additive. Thus prior to the compositions disclosed herein protection of all fuels of interest required more than one additive. Also many anti-static agents are produced from expensive chemicals which render the use of these agents uneconomical.

Accordingly, there is a need for additives and additive mixtures which are easily produced and blended having high, cost effective activity in a broad spectrum of fuels suffering from the danger of explosions and fire caused by static discharge. Additives which can be blended fuels in low concentrations and provide protection from fire and explosion are needed.

The general object of this invention is to provide new classes of anti-static additives. Another object of the invention is to provide additive compositions which have beneficial and cost-effective activity in the broad spectrum of fuels which suffer from the danger of explosion caused by static discharges. Another object of this invention is to provide anti-static additives which are aminomethylene sulfonic acid and synergistic mixtures of aminomethylene sulfuric acids and amine-compound adducts of maleic anhydride-olefin copolymers which are simple to produce and are simple to blend into the fuels of interest.

The objects of this invention can be attained with (1) an aminomethylene sulfonic acid type product of the reaction comprising an amine compound (eg) either a substituted succinimide containing free primary or secondary nitrogen atoms or a compound of the formula $RNH_2$ or $R_1NHCH_2CH_2CH_2NH_2$ wherein R and $R_1$ contain 1 to 25 carbon atoms; a compound of the formula

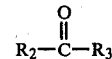

wherein $R_2$ is a hydrogen or a methyl group and $R_3$ is a hydrogen or an alkyl group having from about 1 to 7 carbon atoms and sulfur dioxide; or (2) an aminomethylene sulfonic acid product of the reaction comprising crosslinking an amine compound such as a substituted succinimide containing free primary or secondary nitrogen atoms with a polyfunctional cross-linking agent, and reacting the crosslinked amine with a compound of the formula

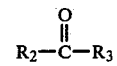

wherein $R_2$ is a hydrogen atom or a methyl group and $R_3$ is a hydrogen atom or an alkyl group having about 1 to 7 carbon atoms; or (3) a mixture of about 100 parts of the aminomethylene sulfonic acid reaction product and from about 1 to 10 parts of adduct of a maleic anhydride olefin copolymer and an amine-compound of the formula

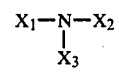

where $X_1$, $X_2$ and $X_3$ are independently a hydrogen atom or a hydrocarbyl group of 1 to 20 carbon atoms. These anti-static agents are relatively stable in the monomeric and polymeric form and in mixtures, and have high activities in fuels which are susceptible to static discharge problems. Furthermore, the monomeric-type compounds can be used as precursors for the polymeric-type anti-static compositions and blends. The crosslinking of the active aminomethylene sulfonic acid antistatic additive enhances the properties of the additives, and the mixtures of the aminomethylene sulfonic acid anti-static additive with a maleic anhydride 1-olefin copolymer amine compound adduct produces a mixture with significantly enhanced activity.

In one aspect this invention is an aminomethylene sulfonic acid.

In a second aspect this invention is an aminomethylene sulfonic acid which is crosslinked.

In a third aspect this invention is a mixture of an aminomethylene sulfonic acid and an amine compound adduct of a maleic anhydride olefin copolymer.

In a fourth aspect this invention is a fuel containing an aminomethylene sulfonic acid anti-static agents or synergistic mixtures of the aminomethylene sulfonic acid and the aminocompound adduct of the maleic anhydride olefin copolymer.

Briefly, the aminomethylene sulfonic acids are produced by reacting an amine compound (eg) a substituted succinimide containing free primary or secondary nitrogen atoms or a compound of the formula $RNH_2$ $R_1NHCH_2CH_2CH_2NH_2$ wherein R and $R_1$ have 1 to 25 carbon atoms with a carbonyl compound and sulfur dioxide. The compounds of this invention cannot be represented by an exact structural formulae since each reagent used in the synthesis can react at different active sites (generally nitrogen atoms) on different molecules.

Amine-compounds which can be used to prepare the aminomethylene sulfonic acids are primary monoamines polyamines, preferably alkylene polyamines and polyalkylene polyamines. Examples of such amines are primary amines of the formula $R—NH_2$ wherein R has 1–25 carbon atoms and is methyl amine, ethyl amine, propyl amine, isopropyl amine, butyl amine, t-butyl amine, oleyl amine, Pentacosenyl amine, etc., ethylene diamine, 2-aminoethyl piperazine, diethylene triamine, di(trimethylene) triamine, dipropylene triamine, triethylene tetraamine, tripropylene tetraamine, tetraethylene pentamine, pentaethylene hexamine, etc. Amines having 12–25 carbon atoms and polyamines having 4–6 amine nitrogens are preferred for maximum antistatic activity in the noncrosslinked anti-static agents.

Amines having the structure $R_1NH—CH_2CH_2CH_2—NH_2$ are sold under the name "Duomeen" which includes "Duomeen CD, T, O, and L-15." These are commercial nitrogen-containing compounds made by the Armak Company. The compounds are made by hydrogenating the adduct produced by the reaction of an amine containing up to 25 carbon atoms, preferably 12–25, and acrylonitrile. The reaction product is a n-monoalkyl-1,3-propylene diamine. For example, "Duomeen CD" is the distilled hydrogenated cocoamine adduct of acrylonitrile. Cocoamine is a $C_{12-14}$ primary hydrocarbon amine, with small amounts of other primary amines. "Duomeen O" is a hydrogenated adduct of an amine and acrylonitrile, wherein the amine is a primary amine having about 18 carbon atoms and is unsaturated. Duomeen T is the hydrogenated adduct of talloamine and acrylonitrile. Talloamine is a mixture of $C_{18}$, $C_{16}$, and $C_{14}$ hydrocarbon amine. As indicated above Duomeens have the general formula $R_1—NH—CH_2CH_2CH_2—NH_2$ wherein R has 1–25 carbon atoms.

The preferred adduct of acyclic hydrocarbyl succinic anhydride and polyamines are based on diethylenetriamine, triethylenetetramine, and tetraethylenepentamine. These polyamines are especially preferred due to the low cost, high activity of resulting anti-static additive and reactivity of the amino nitrogens. Acyclic hydrocarbyl succinic anhydrides having an aliphatic carbon chain from about 12 to 100 carbon atoms, preferably 12–25, in the hydrocarbon substituent are preferred. The molecular weight of the hydrocarbyl group on the succinic anhydride is about 180 to about 1200, preferably 180–380 to produce monomeric anti-static additive of highest activity.

Hydrocarbyl substituted succinic anhydride can be produced by the reaction of maleic anhydride and a polyalkene in an "ENE" reaction or in the reaction of a chlorinated polyalkene with succinic anhydride. The reaction between a straight chain paraffin and maleic anhydride also produces an alkyl succinic anhydride with somewhat lower yields. The polyalkene is produced from ethene, propene, butene, or mixtures thereof. These reactions are well known in the art.

The adduct of hydrocarbyl succinic anhydride and polyamine is generally a mixture of imides and amides. The molecular structure of an alkyl or alkenyl succinimide (I) and succinamide (II) is represented by the following formula:

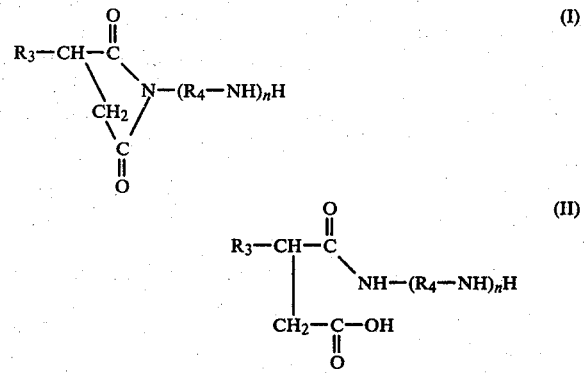

wherein $R_3$ is an alkyl or alkenyl group having 12–100 carbon atoms and $R_4$ is an alkylene group having 2–4 carbon atoms. Generally, the reaction product of an amine and hydrocarbyl succinic anhydride will be referred to as a hydrocarbyl succinimide, although lesser amounts of hydrocarbyl succinamide, structure (II), are generally present. These compounds are also well known in the art.

The carbonyl compounds which react with sulfur dioxide to form sulfonic acid groups are low molecular weight carbonyl compounds having the structure

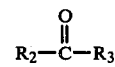

wherein $R_2$ is methyl group or hydrogen atom and $R_3$ is hydrogen atom or alkyl group from 1 to 7 carbon atoms. Aldehydes are preferred, particularly acetaldehyde and most particularly formaldehyde, for ease of reactivity. Examples of such carbonyl compounds include formaldehyde, acetaldehyde, propionaldehyde, butyraldehyde, isobutyraldehyde, heptaldehyde, acetone, methylethyl ketone, methyl isobutyl ketone, etc.

The aldehydes can be used in the monomeric or polymeric form. Linear and cyclic polyaldehydes are formed by polymerization of aldehydes in the presence of dilute catalyst. Paraformaldehyde can be formed by the action of dilute catalyst on formaldehyde resulting in a solid cyclic trimer of formaldehyde, named trioxane or commonly paraformaldehyde. Paraformaldehyde, formaldehyde and trioxane are preferred reagents ($R_2$ and $R_3$ are both hydrogen) due to the ease of handling, reactivity of the reagents and clarity of the products.

In somewhat greater detail, to produce the non-crosslinked aminomethylene sulfonic acid type anti-static compound, 0.5 to 1.5 moles of the carbonyl compound are added per mole of amine compound. The mixture is stirred until clear at a temperature about room temperature (10° C.) to about 160° C. Sulfur dioxide is then introduced into the mixture. This reaction is also exothermic and preferably the temperature is maintained at between about room temperature and 160° C. About 0.1-2.0 moles of sulfur dioxide is added per mole of amine compound.

Briefly, crosslinked aminomethylene sulfonic acid anti-static agents are produced by reacting an amine compound with a polyfunctional crosslinking agent and then reacting the crosslinked amine with a carbonyl compound and sulfur dioxide, or by reacting the non-crosslinked aminomethylene sulfonic acid with a polyfunctional crosslinking agent.

Crosslinking agents contain two or more groups which are capable of reacting with and linking amine compounds. The primary or secondary nitrogen atoms of two amine compound molecules react with a polyfunctional crosslinking agent forming amido, imido, amino and urethanetype links. This crosslinking reaction can be performed prior to, or subsequent to producing the amino methylene sulfonic acid the reaction of the amine compound, the carbonyl compound, and the sulfur dioxide. For example, amine containing primary and secondary nitrogen atoms can react with a crosslinking agent prior to further reaction, or the aminomethylene sulfonic acid can be crosslinked through the free amine groups in the molecule. The crosslinking reaction and the reaction of the carbon compound and sulfur dioxide can occur at any primary or secondary nitrogen atom in the amine, and in this way the crosslinking agent can form large crosslinked units. The amine compound contains on an average at least two secondary or primary nitrogen atoms, one for the crosslinking reaction, and one for the methylene sulfonic acid reaction.

Examples of polyfunctional compounds reactive with the amine nitrogens are dicarboxylic acid anhydrides, dicarboxylic acid chlorides, hydrocarbyl diisocyanate, and epihalorohydrin, alkylene dihalides, diepoxides, etc. Dicarboxylic acid chlorides include, oxaloyl dichloride, succinoyl dichloride, adipoyl dichloride, and terephthaloyl dichloride. Hydrocarbyl diisocyantes include, 1,6-heptane-diisocyanate, 1,6-hexane-diisocyanate, 1,4-butane diisocyanate, and 1,2-ethane diisocyanate, benzene diisocyanate, and toluene diisocyanate and other substituted aromatic diisocyanates. The ease of reactivity, low cost, and high activity of the resulting anti-static compounds make toluene diisocyanate and 1,6-hexane diisocyanate the preferred crosslinking agents. When diisocyanate is used as a crosslinking agent the product can be thought of as a urethane type polymer.

Amine compounds which can be used to prepare the crosslinked aminomethylene sulfonic acid or an adduct of the succinic anhydride which can be used to prepare the crosslinked antistatic agent are diamines, triamines, and polyamines, etc., preferably alkylene polyamines and polyalkylene polyamines. Examples of such amines are ethylene diamine, 2-aminoethyl piperazine, diethylene triamine, di(trimethylene)triamine, dipropylene triamine, triethylene tetraamine, tripropylene tetraamine, tetraethylene pentamine, pentaethylene hexamine, etc. Amines having 4-6 amine nitrogens are preferred for the high anti-static activity and ease of reactivity.

A preferred amine compound for the crosslinked aminomethylene sulfonic acid is an adduct of a hydrocarbyl substituted succinic anhydride and an amine or polyamine selected from those discussed above. Polyamines such as, diethylene triamine, triethylene tetraamine, and tetraethylene pentamine are especially preferred due to the low cost, high activity of resulting anti-static additive and reactivity of the amino nitrogens. Hydrocarbyl substituted succinic anhydrides used for the monomeric type additives have from about 12 to 100 carbon atoms, or preferably about 12-40 carbon atoms. The molecular weight of the alkyl or alkenyl group on the succinic anhydride used to produce polymeric type additive is about 200 to about 1200, preferably 200-600.

The carbonyl compounds used to make the crosslinked aminomethylene sulfonic acid are the same as those for the noncrosslinked aminomethylene sulfonic acid.

In somewhat greater detail, the crosslinked aminomethylene sulfonic acid anti-static agents are produced by adding slowly to the amine about 0.5 to 1.5 equivalents of the cross-linking agent per equivalent of amine compound at a temperature about room temperature to 160° C. Preferably, the reaction is quickly brought to completion generally within 1 to 2 hours with maximum yield when conducted at a temperature of about 60° C. to 120° C.

At the conclusion of the cross-linking reaction, the mixture is cooled. About 0.1 to 1.5 equivalents of the carbonyl compounds per equivalent of the amine is added to the cross-linked amine. The mixture is stirred until clear at a temperature of about 40° C. to about 200° C. Sulfur dioxide is then introduced into the mixture. This reaction is exothermic and preferably the temperature is maintained at between about room temperature to 160° C. About 0.1-2.0 equivalents of sulfur dioxide is added per mole of amine compound. Optionally, an excess of sulfur dioxide gas is passed into the reaction.

Alternatively about 0.5 to 1.5 equivalents of the crosslinking agent can be added to the aminomethylene sulfonic acid per equivalents of amine compound at a temperature from about room temperature (10° C.) to about 160° C. for about 1 to 2 hours.

The solvents useful in this invention are inert to sulfur dioxide, amino-containing compounds, and carbonyl-containing compounds. Hydrocarbon aromatics solvents such as benzene and xylene, etc., and other hydrocarbons such as hexane, petroleum ether and petroleum distillates are suitable solvents.

The preferred solvents are aromatic compounds. One preferred aromatic solvent is a $C_9+$ aromatic solvent. This solvent is a mixture of hydrocarbons resulting from a refinery stream containing aromatic compounds containing 9 carbon atoms and greater having a boiling point from about 150° C. (300° F.)-200° C. (390° F.) 95%. This solvent is well known to the petroleum industry.

The anti-static amino methylene sulfonic acid type additives can be prepared in batch or continuous processes. In batch processes, the solvent solution of reactants or the reactants without solvent may be added to the other reactants in a suitable vessel. In continuous processing, two components in solution or solvent can be charged to different (countercurrent process) or the same reaction zone, e.g., the upper end of a vertical zone maintained at a suitable temperature. The product commonly is withdrawn from the other end into purification or storage.

Briefly, an effective anti-static composition can be prepared by forming a composition containing about 1 to 100 parts by weight of an aminomethylene sulfonic acid and about 1 part of an amine compound adduct of a maleic anhydride olefin copolymer. Suitable maleic anhydride-olefin copolymers are made by reacting approximately equimolar amounts of an 1-olefin and maleic anhydride under conventional free radical conditions. These polymers and their synthesis are well known. Olefins useful in this invention are alpha-olefins, 1-olefins such as ethene, propene, 1-butene, 1-pentene, 1-hexene, 1-heptene, 1-octene, 1-octadecene, 1-eicosene, etc.

Further detail of the production of the maleic anhydride olefin copolymer and the subsequent amine compound adduct are found in U.S. Pat. No. 3,003,858, which is incorporated by reference. The preferred maleic anhydride olefin copolymer has a molecular weight from about 2000 to 8000 preferably 4500–6500 and is made from 1-octadecene and maleic anhydride. This coppolymer is preferred for the low cost, high activity, and ease of preparation of the components.

The maleic anhydride-olefin copolymer adduct is formed in the reaction with amine-compound such as ammonia, primary, secondary or tertiary amines of the formula

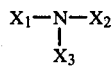

wherein $X_1$, $X_2$ and $X_3$ are independently hydrogen or straight or branched chain alkyl group with 1 to 29 carbon atoms. Examples of suitable amine-compounds are ammonia, methyl amine, ethyl amine, isopropyl amine, n-butyl amine, dibutyl amine, t-butyl amine, octadecyl amine, eicosyl amine, dimethyl amine, diethyl amine, methyl isobutyl amine, ethyl isopropyl amine, dioctadecyl amine, trimethyl amine, triethyl amine, triisoamyl amine, trioctadecyl amine, and trieicosyl amine.

The adduct of the amine-compound and the maleic anhydride olefin copolymer contains amide and possibly some imide linkages with the anhydride function on the polymer. The exact nature of the reaction product of the tertiary amine maleic anhydride polymer is unknown, although spectrographic studies show amide type bonding. This reaction is well known in the art. The adduct is formed by dissolving or suspending the copolymer in a hydrocarbon solvent medium. The solution can be heated from about room temperature to reflux temperature, about 100° C., and the amine compound is added to the mixture until no further reaction continues, about 2 hours. The mixture was cooled, filtered, and is ready for use.

The effective mixtures of the crosslinked aminomethylene sulfonic acid and the amine compound adduct of the maleic anhydride 1-olefin copolymer contains about 1 to 100 parts of the polymeric-type sulfonic acid for each part of the amine compound maleic anhydride olefin copolymer adduct. These mixtures are advantageously made in a hydrocarbon carrier fluid such as a light fraction, kerosene, lubricating oil, toluene, xylene, $C_9+$ aromatics, etc.

The aminomethylene sulfonic acid or mixture with the polymer adduct in a solvent can be blended into the fuel of interest in concentration of from about 0.1 to 10.0 parts of additive per million parts of fuel based on the neat polymer.

Electrical terms which define conductivity are the siemen and the MHO. The practical units are the picosiemen. One picosiemen is equal to $10^{-14}$ MHO per centimeter or $10^{-14}$ per OHM centimeter. Generally a conductivity greater than about 50 picosiemen/meter are necessary to dissipate static electricity.

A field of specific applicability of the present invention is in the improvement of organic liquid compositions in the form of petroleum distillate fuel oils having an initial boiling point from about 75° F. to about 135° F. and an end boiling point from about 250° F. to about 1000° F. It should be noted, in this respect, that the term "distillate fuel oils" is not intended to be restricted to straightrun distillate fractions. These distillate fuel oils can be straightrun distillate fuel oils, catalytically or thermally cracked (including hydrocracked) distillate fuel oils, or mixtures of straightrun distillate fuel oils, naphthas and the like, with cracked distillate stocks. Moreover, such fuel oils can be treated in accordance with well-known commercial methods, such as acid or caustic treatment, hydrogenation, solvent refining, clay treatment, and the like. Distillate fuels are characterized by their relatively low viscosity, pour point and the like. The principal property which characterizes these contemplated hydrocarbons, however, is their distillation range. As hereinbefore indicated, this range will lie between about 75° F. and about 1000° F. Obviously, the distillation range of each individual fuel oil will cover a narrower boiling range, falling nevertheless within the above-specified limits. Likewise, each fuel oil will boil substantially continuously, throughout its distillation range. Particularly contemplated among the fuel oils are Nos. 1, 2 and 3 fuel oils, used in heating and diesel fuel oils, gasoline, turbine fuels and the jet combustion fuels, as previously indicated. The domestic fuel oils generally conform to the specifications set forth in ASTM Specification D396-48T. Specifications for diesel fuels are defined in ASTM Specification D-975-48T. Typical jet fuels are defined in Military Specification MIL-F-56248.

EXAMPLE 1

27.0 grams of "Duomeen T" (0.075 moles) a hydrogenated tallow amine derivative of acrylonitrile, and 2.25 grams of paraformaldehyde (0.075 moles) were placed in a 300 ml. three-neck flask with 100 ml. of benzene (tallow amine is a natural amine of about 18 carbon atoms) having the theoretical structure $CH_3(CH_2)_{17}-NH-(CH_2)_3-NH_2$. The mixture was heated to a temperature from about 55° C. to about 60° C. and 0.075 moles of sulfur dioxide was passed into the liquid in about 30 minutes. 34.0 grams of 5 W oil was added to the clear mixture and benzene was removed from the mixture by heating. The product was approximately 50 percent additive, based on the oil.

EXAMPLE 2

27.0 grams of 37 Duomeen O" (0.075 moles) the hydrogenated adduct of n-oleyl amine and acrylonitrile having a theoretical structure $CH_3(CH_2)_7Ch=CH(CH_2)_8NH(CH_2)_3NH_2$ and 2.25 grams mole of paraformaldehyde (0.075 moles) were placed in a 300 ml. three-neck flask with 100 ml. of benzene. The mixture was heated to a temperature from about 55° C. to about 60° C. and 0.075 moles of sulfur dioxide was passed into the liquid in about 30 minutes. 34.0 grams of 5 W oil was added to the clear mixture and benzene was removed from the mixture by heating. The product was approximately 50 percent additive, based on the oil.

EXAMPLE 3

5.6 grams of diethylenetriamine and 34.4 grams of polybutenyl succinic anhydride in which the polybutyl group has a molecular weight about 450 are placed in 100 ml. of xylene in a round bottom flask with a reflux condenser and a nitrogen atmosphere. The mixture is heated to reflux for 3 hours. The solvent is removed and the adduct is recovered by distillation up to a temperature of 380° F.

40 grams of polybutenyl succinimide adduct and 1.53 grams of paraformaldehyde was placed in a 300 ml. three-neck flask with 100 ml. of benzene. The mixture was heated to a temperature of about 55° C. to about 60° C. and 0.075 moles of sulfur dioxide passed into the liquid in about 30 minutes. 34 grams of 5 W oil was added to the clear mixture and the benzene was removed from the mixture. The product was approximately 50 percent additive, based on oil.

EXAMPLE 4

6.647 g. triethylenetetramine is treated with 30 grams polybutyl succinic anhydride (0.04545 mole) in 50 ml. of $C_9+$ in the same manner as in Example 1 forming a triethylene tetraamine adduct of polybutenyl succinic anhydride.

One mole equivalent of polybutenyl succinimide adduct and 3 mole equivalents of paraformaldehyde was placed in a 300 ml. three-neck flask with 100 ml. of benzene. The mixture was heated to a temperature of about 55° C. to about 60° C. and about 1 mole equivalent of sulfur dioxide was passed into the liquid until absorption of the gas ceases about 30 minutes. 34 grams of 5 W oil was added to the clear mixture and the benzene was removed from the mixture. The yield of product was about 100 percent of theoretical. The product was approximately 50 percent additive, based on the oil.

EXAMPLE 5

Example 1 was repeated except substituting one mole of oleyl amine and one mole of formaldehyde for the "Duomeen T" and the paraformaldehyde.

EXAMPLE 6

Example 1 was repeated except substituting one mole of "Duomeen L-15" and one mole of formaldehyde for the "Duomeen T" and the paraformaldehyde.

EXAMPLE 7

Example 1 was repeated except substituting one mole of "Duomeen L-15" and one mole of propaldehyde for the "Duomeen T" and the paraformaldehyde.

EXAMPLE 8

Example 1 was repeated except substituting one mole of "Duomeen L-15" and one mole of heptaldehyde for the "Duomeen T" and the paraformaldehyde.

EXAMPLE 9

Example 1 was updated except substituting one mole of "Duomeen O" and one mole of formaldehyde for the "Duomeen T" and the paraformaldehyde.

EXAMPLE 10

Example 1 was repeated except substituting one mole of "Duomeen O" and one mole of propaldehyde for the "Duomeen T" and the paraformaldehyde.

EXAMPLE 11

Example 1 was repeated except substituting one mole of "Duomeen O" and one mole of acetaldehyde for the "Duomeen T" and the paraformaldehyde.

EXAMPLE 12

Example 1 was repeated except substituting one mole of oleyl amine for the "Duomeen T."

EXAMPLE 13

Example 1 was repeated except substituting one mole of formaldehyde for the paraformaldehyde.

EXAMPLE 14

Example 1 was repeated except substituting one mole of propaldehyde for the paraformaldehyde.

EXAMPLE 15

Example 1 was repeated except substituting one mole of heptaldehyde for the paraformaldehyde.

EXAMPLE 16

Example 1 was repeated except substituting one mole of acetaldehyde for the paraformaldehyde.

EXAMPLE 17

Example 4 was repeated except substituting one mole equivalent of formaldehyde for the paraformaldehyde.

EXAMPLE 18

Example 3 was repeated except substituting 2 mol equivalent of formaldehyde for the paraformaldehyde.

EXAMPLE 19

Example 3 was repeated except substituting 3 moles of formaldehyde for the paraformaldehyde.

EXAMPLE 20

Example 3 was repeated except substituting 1 mole of acetaldehyde for the paraformaldehyde.

EXAMPLE 21

Example 3 was repeated except substituting 2 moles of acetaldehyde for the paraformaldehyde.

EXAMPLE 22

Example 3 was repeated except substituting 3 moles of acetaldehyde for the paraformaldehyde.

EXAMPLE 23

Example 3 was repeated except substituting one mole of formaldehyde for the paraformaldehyde.

EXAMPLE 24

Example 3 was repeated except substituting 1.5 moles of formaldehyde for the paraformaldehyde.

EXAMPLE 25

Example 3 was repeated except substituting 2.0 moles of formaldehyde for the paraformaldehyde.

EXAMPLE 26

Example 3 was repeated except substituting 2.5 moles of formaldehyde for the paraformaldehyde.

EXAMPLE 27

Example 3 was repeated except substituting 3.0 moles of formaldehyde for the paraformaldehyde.

EXAMPLE 28

30.0 g. of polybutenyl succinic anhydride having a molecular weight of about 660 (about 0.045 moles) was added to 6.65 g. of triethylenetetraamine (about 0.045 moles) in 50 cc. of a $C_9+$ aromatic solvent in a flask equipped with a stirrer and a nitrogen stream. The water of reaction was removed under a nitrogen stream at a temperature of 180° C. for 1.5 hours forming a succinimide adduct.

To this adduct was added 7.5 g. of 1,6-hexane diisocyanate (about 0.045 moles) dissolved in 50 cc. of $C_9+$ aromatic solvent at 85° C. The solution was heated to a temperature of 120° C. for 2 hours and then cooled to 85° C. and 1.3634 g. of paraformaldehyde (about 0.045 moles) was added. The mixture was stirred at 85° C. until it was clear (about 30 minutes). 0.045 moles of $SO_2$ was introduced at a temperature between 85° and 95° C. for 3 hours.

EXAMPLE 29

Example 28 was repeated, except with 30 g. of the polybutyl succinic anhydride, 6.64 g. of triethylenetetramine, 7.91 g. of toluene diisocyanate, 1.365 g. of paraformaldehyde, and 2.6 gm $SO_2$.

EXAMPLE 30

Example 28 was repeated, except with 20 g. of the polybutenyl succinic anhydride, 0.040 moles molecular weight about 500 was reacted with 5.85 g. triethylene tetramine, 6.96 g. of toluene diisocyanate, 1.0 g. of paraformaldehyde, and 2.6 gm $SO_2$.

EXAMPLE 31

Example 28 was repeated, except with 20 g. of the polybutenyl succinic anhydride, molecular weight about 500 (about 0.04 moles), 5.85 g. triethylenetetramine, 6.728 g. of 1,6-hexane diisocyanate, 1.0 g. of formaldehyde, and 2.6 gm $SO_2$.

EXAMPLE 32

Example 28 was repeated, except with 20 g. of the polybutenyl succinic (about 0.04 moles) anhydride, molecular weight about 500, 5.62 g. triethylene tetramine, 6.469 g. of 1,6-hexane diisocyanate, 1.155 g. of paraformaldehyde, and 2.6 gm $SO_2$.

EXAMPLE 33

Example 28 was repeated, except with 20 g. of the polybutenyl succinic anhydride, (about 0.04 moles) molecular weight about 500, 5.571 g. triethylenetetramine, 6.407 g. of 1,6-hexane diisocyanate, 1.144 g. of paraformaldehyde, and 2.6 gm $SO_2$.

EXAMPLE 34

Example 28 was repeated in a series of reactions substituting 20 g. of polybutenyl succinic anhydride molecular weight about 500, 5.2 gm of triethylenetetramine 1,6-hexane diisocyanate, 1.44 g. of paraformaldehyde, and $SO_2$ (excess) mole ratio of 1,6-hexane diisocyanate to mole of triethylenetetramine was varied as shown below.

Mole Ratio 1,6 Hexane Diisocyanate/TETA a: 0.0
b: 0.2
c: 0.6
d: 0.8
e: 0.9
f: 0.95
g: 1.00

EXAMPLE 35

30.0 g. of polybutenyl succinic anhydride, molecular weight about 660, was added to 5.65 g. of triethylenetetramine in 50 ml. of a $C_9+$ aromatic solvent and heated to 180° C. for 30 minutes. The solution was cooled to 35° and 100 ml. of solvent was added. 6.394 g. of toluene diisocyanate was added slowly and the solution was heated to 160° C. for 2 hours. The solution was cooled to 85° C. and 1.1845 g. of paraformaldehyde was added. The solution was held at 85° C. and stirred until clear, approximately 30 minutes. 2.6 gm $SO_2$ was sparged through the solution for 2.5 hours at 85° C.

EXAMPLE 36

Example 35 was repeated except with 30 g. of polybutenyl succinic anhydride, molecular weight about 500, 5.98 g. of triethylenetetramine, 6.055 g. of toluene diisocyanate, 1.228 g. of formaldehyde, and 2.6 gm $SO_2$.

EXAMPLE 37

Example 35 was repeated except with 30 g. of polybutenyl succinic anhydride, molecular weight about 500, 5.807 g. of triethylenetetramine, 6.57 g. of toluene diisocyanate, 1.192 g. of paraformaldehyde, and 2.6 gm $SO_2$.

EXAMPLE 38

Example 35 was repeated except with 30.0 gm polybutyl succinic anhydride, molecular weight about 540, 4.875 gm TETA, 5.799 gm TDI, and 1.00 g paraformaldehyde.

EXAMPLE 39

Example 35 was repeated except with 22.58 grams of polybutenyl succinic anhydride (0.044 M) molecular weight about 512, 5.48 gm triethylenetetraamine (TETA) (0.037 m), 6.53 toluene diisocyanate (TDI) (0.037 m), 1.125 gm formaldehyde (0.037 m) and 2.40 gm of sulfur dioxide ($SO_2$ 0.037 m).

EXAMPLE 40

Example 29 was repeated except with 5.81 gm TETA (0.039 m) 6.92 gm TDI (0.040 m), 1.192 gm formaldehyde (0.040 m) and 2.541 gm $SO_2$ (0.040 m).

EXAMPLE 41

Example 35 was repeated except with 24.91 gm polybutenyl succinic anhydride (molecular weight 564.8) (0.044 m), 5.48 gm TETA (0.037 m), 6.53 TDI (0.037 m), 1.125 gm formaldehyde (0.037 m) and 2.39 gm $SO_2$ (0.037 m).

EXAMPLE 42

Example 40 was repeated except with 5.81 gm TETA (0.039 m) 6.92 gm TDI (0.040 m), 1.1920 gm formaldehyde (0.040 m) and 2.541 gm $SO_2$ (0.040 m).

EXAMPLE 43

Example 35 was repeated except with 24.41 gm polybutenyl succinic anhydride (molecular weight 554.9) (0.044 m), 5.48 gm TETA (0.037 m), 6.53 TDI (0.037 m), 1.1253 gm formaldehyde (0.037 m) and 2.40 gm sulfur dioxide (0.037 m).

EXAMPLE 44

Example 42 was repeated except with 5.81 gm TETA (0.040 m) 6.92 gm TDI (0.040 m), 1.1920 gm formaldehyde (0.040 m) and 2.541 gm $SO_2$ (0.040 m).

EXAMPLE 45

Example 35 was repeated except with 25.48 gms polybutenyl succinic anhydride (molecular weight 578) (0.044 m), 5.48 gm TETA (0.037 m), 6.53 TDI (B 0.037 m), 1.1253 gm formaldehyde (0.037 m) and 2.4 gm sulfur dioxide (0.037 m).

EXAMPLE 46

Example 44 was repeated except with 5.81 gm TETA (0.04 m) 6.92 gm TDI (0.040 m), 1.1920 gm formaldehyde (0.040 m) and 2.54 gm $SO_2$ (0.040 m).

EXAMPLE 47

Example 35 was repeated with 30.0 gm polybutenyl succinic anhydride.

EXAMPLE 48

20 gm of maleic anhydride octadecene copolymer, molecular weight about 5600 was dissolved in 200 ml of toluene and 10 ml of $H_2O$ added in a 500 ml round bottom flask with a reflux condenser. The emulsion was heated to 65° C. Anhydrous ammonia gas was heated at reflux for three hours then cooled and filtered. More toluene was added to reduce the viscosity of the solution at room temperature. The resulting solution in toluene was 14.16% by weight product.

EXAMPLE 49

10 gm of a maleic anhydride 1-octadiene copolymer, molecular weight 5600, was reacted with 4.17 g n-butyl amine in 200 ml of toluene at 100° C. for two hours in a 500 ml round bottom flask with a reflux condenser, then at reflux for two hours until no water or amine distilled. The resulting solution was 6.88% by weight product in toluene.

EXAMPLE 50

10 gm of a maleic anhydride 1-octadiene copolymer, molecular weight about 5600, was dissolved in 150 ml of xylene and heated to 90° C. in a 500 ml round bottom flask with a reflux condenser. The solution was heated at 150° for four hours.

EXAMPLE 51

10 gm of a maleic anhydride 1-octadiene copolymer, molecular weight about 5600, was dissolved in 200 ml xylene in a 500 ml round bottom flask. 2.5 gm of isoamyl alcohol and 6.67 triisoamyl amine were added. The solution was heated for eight hours at reflux. The solution was cooled.

TABLE I

Conductivity of Jet Fuel Containing Monomeric-Type Additive

| Product in Example No. | Concentration (PPM) in JP-4 Jet Fuel at 20° C. for Activity of 50 picosiemens/meter |
|---|---|
| 1 | 1.0 |
| 2 | 5.9 |
| 3 | 3.3 |
| 4 | 2.0–3.0 |
| 5 | 13.0 |
| 6 | 6.7 |
| 7 | 4.25 |
| 8 | 3.3 |
| 9 | 5.9 |
| 10 | 8.0 |
| 11 | 2.1 |
| 12 | 13 |
| 13 | 1.0 |
| 14 | 7.0 |
| 15 | 4.3 |
| 16 | 2.3 |
| 17 | 4.0 |
| 18 | 6.0 |
| 19 | 4.0 |
| 20 | 10.0 |
| 21 | 10.0 |
| 22 | 10.0 |
| 23 | 4.0 |
| 24 | 5.1 |
| 25 | 2.0–3.0 |
| 26 | 2.0–3.0 |
| 27 | 2.0–3.0 |

TABLE II

CONDUCTIVITY OF #2 FUEL CONTAINING POLYMERIC-TYPE ADDITIVE

| Product in Example | Conc (PPM) | (piscosiemen/meter) |
|---|---|---|
| 28 | 2 | 94.6 |
| 29 | 10 | 103 |
| 30 | 10 | 49 |
| 31 | 10 | 100 |
| 32 | 10 | 155 |
| 33 | 10 | 168 |
| 34a | 10 | 104 |
| b | 10 | 117 |
| c | 10 | 144 |
| d | 10 | 176 |
| e | 10 | 108 |
| f | 10 | 132 |
| g | 10 | 98 |
| 35 | 10 | 305 |
| 36 | 10 | 193 |
| 37 | 10 | 363 |
| 38 | 10 | 194 |

TABLE III

Conductivity of #2 Heating Fuel Containing Mixture of Polymeric-Type Additives

| Additive (Conc., ppm based on neat additive) | Conductivity of Fuel picosiemens/ meter at 74° F. |
|---|---|
| Base Fuel | 21.0 |
| Example 39 (10 ppm) | 211.0 |
| Example 40 (10 ppm) | 197.0 |

TABLE III-continued

Conductivity of #2 Heating Fuel
Containing Mixture of Polymeric-Type Additives

| Additive (Conc., ppm based on neat additive) | Conductivity of Fuel picosiemens/ meter at 74° F. |
|---|---|
| Example 41 (10 ppm) | 224.0 |
| Example 42 (10 ppm) | 158.0 |
| Example 43 (10 ppm) | 227.0 |
| Example 44 (10 ppm) | 210.0 |
| Example 45 (10 ppm) | 262.0 |
| Example 46 (10 ppm) | 219.0 |
| Example 47 (10 ppm) | 175.0 |
| Example 48 (10 ppm) | 184.0 |
| Example 49 (10.0 ppm) | 175.0 |
| Example 50 (1.0 ppm) | 33.0 |
| Example 51 (1.0 ppm) | 45.0 |
| Example 45 (10 ppm) + Example 48 (1.0 ppm) | 894.0 |
| Example 45 (10 ppm) + Example 48 (2.0 ppm) | 1216.0 |
| Example 45 (1 ppm) + Example 48 (0.1 ppm) | 92.0 |
| Example 45 (10 ppm) + Example 49 (1 ppm) | 1002.0 |
| Example 45 (10 ppm) + Example 49 (2 ppm) | 1369.0 |
| Example 39 (10 ppm) + Example 48 (1 ppm) | 661.0 |
| Example 39 (10 ppm) + Example 48 (2 ppm) | 1094.0 |
| Example 40 (10 ppm) + Example 48 (1 ppm) | 743.0 |
| Example 40 (10 ppm) + Example 48 (2 ppm) | 1142.0 |
| Example 39 (10 ppm) + Example 49 (1 ppm) | 778.0 |
| Example 39 (10 ppm) + Example 49 (2 ppm) | 1216.0 |
| Example 40 (10 ppm) +. Example 49 (1 ppm) | 516.0 |
| Example 40 (10 ppm) + Example 49 (2 ppm) | 1251.0 |
| Example 41 (10 ppm) + Example 49 (1 ppm) | 919.0 |
| Example 41 (10 ppm) + Example 49 (2 ppm) | 1263.0 |
| Example 42 (10 ppm) + Example 49 (1 ppm) | 533.0 |
| Example 42 (10 ppm) + Example 49 (2 ppm) | 973.0 |
| Example 41 (10 ppm) + Example 48 (1ppm) | 486.0 |
| Example 41 (19 ppm) + Example 48 (2ppm) | 973.0 |
| Example 42 (10 ppm) + Example 48 (1 ppm) | 529.0 |
| Example 42 (10 ppm) + Example 48 (2 ppm0 | 966.0 |
| Example 43 (10 ppm) + Example 49 (1 ppm) | 859.0 |
| Example 43 (10 ppm) + Example 49 (2 ppm) | 1340.0 |
| Example 44 (10 ppm) + Example 49 (1 ppm) | 919.0 |
| Example 44 (10 ppm) + Example 49 (2 ppm) | 1313.0 |
| Example 43 (10 ppm) + Example 48 (1 ppm) | 486.0 |
| Example 43 (10 ppm) + Example 48 (2 ppm) | 1103.0 |
| Example 44 (10 ppm) + Example 48 (1 ppm) | 612.0 |
| Example 44 (10 ppm) + Example 48 (2 ppm) | 1059.0 |
| Example 46 (10 ppm) + Example (1 ppm) | 560.0 |
| Example 46 (10 ppm) + Example 48 (2 ppm) | 1251.0 |
| Example 46 (10 ppm) + Example 49 (1 ppm) | 516.0 |
| Example 46 (10 ppm) + Example 49 (2 ppm) | 1288.0 |
| Example 47 (10 ppm) + Example 48 (1 ppm) | 435.0 |
| Example 47 (10 ppm) + Example 48 (2 ppm) | 951.7 |
| Example 47 (10 ppm) + Example 49 (1 ppm) | 760.0 |
| Example 47 (10 ppm) + Example 49 (2 ppm) | 1042.0 |

Table I shows the beneficial antistatic activity of the aminomethylene sulfonic acid in some cases as little as 13 ppm provide adequate conductivity. Table II also shows beneficial antistatic activity of the crosslinked aminomethylene sulfonic acid. The crosslinking increases the activity of the agent. Table III shows the great increase produced by the composition comprising the crosslinked antistatic additive and the amine-compound maleic anhydride octadecene copolymer adduct. As little as 1 ppm of the adduct of Example 49 with 10 ppm of the crosslinked aminomethylene sulfonic acid Example 45 gives a conductivity of 1002. The conductivity of Example 49 alone is 175 and the conductivity of Example 45 alone is 262 giving a total expected conductivity of 437. Together the agents more than double the expected value.

Many variations from the examples and illustrations found above are possible. The examples and illustrations shown are to describe specific compositions which were prepared. Those skilled in the art will be able to create many other variations similar to those examples found above. These examples should not be used in determining the scope of this invention.

I claim:

1. An aminomethylene sulfonic acid anti-static composition comprising the reaction product of:
   A. an adduct of a polyamine and a hydrocarbyl succinic anhydride:
   B. about 0.5 to 1.5 equivalents of a carbonyl compound having the formula:

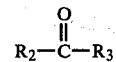

wherein $R_2$ comprises a hydrogen or methyl group and $R_3$ comprises a hydrogen or an alkyl group having 1 to 7 carbon atoms, per equivalent of component A and
   C. about 0.1 to 2.0 equivalents sulfur dioxide per mole of component A.

2. The composition of claim 1 wherein the polyamine is diethylenetriamine, triethylenetetramine or tetraethylenepentamine.

3. The composition of claim 1 wherein the amine is an adduct of a hydrocarbyl succinic anhydride having 12-25 carbon atoms in the hydrocarbyl group.

4. The composition of claim 1 wherein $R_2$ and $R_3$ of the carbonyl compound are hydrogen.

5. A fuel containing 0.1 to 10.0 parts of the aminomethylene sulfonic acid of claim 1 per million parts of fuel.

* * * * *

UNITED STATES PATENT OFFICE
CERTIFICATE OF CORRECTION

Patent No. 4,302,216     Dated November 24, 1981

Inventor(s) James R. Spence

It is certified that error appears in the above-identified patent and that said Letters Patent are hereby corrected as shown below:

Column 1, line 51, "beteropolymer" should read --heteropolymer--.

Column 1, line 59, "these composition" should read --these compositions--.

Column 1, line 65, "costeffective" should read --cost-effective--.

Column 3, line 3, "mixtures" should read --mixture--.

Column 3, line 15, "agents" should read --agent--.

Column 3, line 22, after "$RNH_2$" insert the word --or--.

Column 3, line 26, "formulae" should read --formula--.

Column 3, line 36, "Pentacosenyl" should read --pentacosenyl--.

Column 5, line 30, "urethanetype" should read --urethane-type--.

Column 5, line 32, "amino methylene" should read --aminomethylene--.

Column 5, line 32, "acid the reaction" should read --acid by the reaction--.

Column 5, line 53, "diisocyantes" should read --diisocyanates--.

Column 6, line 55, "aromatics" should read --aromatic--.

Column 6, line 67, "amino methylene" should read --aminomethylene--.

Column 7, line 16, "an 1-olefin" should read --a 1-olefin--.

Column 7, line 22, "detail" should read --details--.

Column 8, line 16, "are" should read --is--.

UNITED STATES PATENT OFFICE
CERTIFICATE OF CORRECTION

Patent No. 4,302,216  Dated November 24, 1981

Inventor(s) James R. Spence

It is certified that error appears in the above-identified patent and that said Letters Patent are hereby corrected as shown below:

Column 8, line 24, "straightrun" should read --straight-run--.

Column 8, line 25, "straightrun" should read --straight-run--.

Column 8, line 27, "straightrun" should read --straight-run--.

Column 9, line 3, "of 37 Duomeen" should read --of "Duomeen--.

Column 9, line 6, that portion of the formula reading "Ch" should read --CH--.

Column 9, line 26, "of polybutenyl" should read --of the polybutenyl--.

Column 12, line 13, "1,6 Hexane" should read --1,6-Hexane--.

Column 13, line 29, "(B 0.037" should read --(0.037--.

Column 13, line 67, after the period, add the following sentence --7.38 gm dibutyl amine (0.73 m) was added to the solution--.

Column 15, line 13, "Example 48 (10 ppm)" in Table III should read --Example 48 (1.0 ppm)--.

Column 15, line 14, "Example 49 (10.0 ppm)" in Table III should read --Example 49 (1.0 ppm)--.

Column 15, line 18, "(0.1)ppm)" in Table III should read --(0.1 ppm)--.

Column 15, line 26, "+." in Table III should read --+--.

Column 15, line 31, "Example 41 (19 ppm)" in Table III should read --Example 41 (10) ppm)--.

UNITED STATES PATENT OFFICE
CERTIFICATE OF CORRECTION

Patent No. 4,302,216              Dated November 24, 1981

Inventor(s) James R. Spence

It is certified that error appears in the above-identified patent and that said Letters Patent are hereby corrected as shown below:

Column 15, line 33, "(2 ppm0)" should read --(2 ppm)--.

Column 15, line 40, "Example (1 ppm)" in Table III should read --Example 48 (1 ppm)--.

Signed and Sealed this

Eighteenth Day of May 1982

[SEAL]

Attest:

GERALD J. MOSSINGHOFF

Attesting Officer      Commissioner of Patents and Trademarks